United States Patent [19]

Baysdon et al.

[11] Patent Number: 5,041,627
[45] Date of Patent: Aug. 20, 1991

[54] PREPARATION OF N-ACYL-AMINOMETHYLPHOSPHONATES

[75] Inventors: Sherrol L. Baysdon, Chesterfield; Donald L. Fields, Jr., Manchester, both of Mo.

[73] Assignee: Monsanto Company, St. Louis, Mo.

[21] Appl. No.: 465,626

[22] Filed: Jan. 19, 1990

Related U.S. Application Data

[63] Continuation of Ser. No. 275,862, Nov. 25, 1988, abandoned.

[51] Int. Cl.$^5$ .............................. C07F 9/38
[52] U.S. Cl. ........................ 562/16; 71/86; 562/15
[58] Field of Search ................... 562/15, 16

[56] References Cited

U.S. PATENT DOCUMENTS

| | | | |
|---|---|---|---|
| 2,304,157 | 12/1942 | Engelmann et al. | 562/15 |
| 2,328,358 | 8/1943 | Pikl | 562/16 |
| 3,961,934 | 6/1976 | Ratts | 562/15 |
| 4,482,504 | 11/1984 | Felix | 562/18 |
| 4,657,705 | 4/1987 | Miller et al. | 260/502.5 |
| 4,830,788 | 5/1989 | Feeman | 562/16 |
| 4,851,159 | 7/1989 | Fields et al. | 562/17 |

FOREIGN PATENT DOCUMENTS 117780  1/1982  Poland .

OTHER PUBLICATIONS

*Synthetic Communications*, Jun. 1978, pp. 479-480, Josef Oleksyszym et al.
*Synthetic Communications*, A Convenient Synthesis of Aminomethylphosphonic Acid, Pulwer, et al, 16(7), 733-739 (1986).
*Journal of Organic Chemistry*, vol. 27, pp. 2067-2070, Extent of Formaldehyde Reaction with Selected Amides, Vail et al.

*Primary Examiner*—J. E. Evans
*Attorney, Agent, or Firm*—Frank D. Shearin

[57] ABSTRACT

N-Acyl-aminomethylphosphonic acids represented by the formula

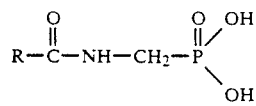

wherein R is selected from the group consisting of methyl and aryl are prepared by:
(a) bringing together under substantially anhydrous reaction conditions an amide represented by the formula

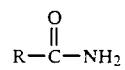

wherein R is as defined above and paraformaldehyde; and thereafter,
(b) adding phosphorous trihalide to the reaction mixture.

12 Claims, No Drawings

PREPARATION OF N-ACYL-AMINOMETHYLPHOSPHONATES

This is a continuation of application Ser. No. 07/275,862, filed on Nov. 25, 1988, now abandoned.

BACKGROUND OF THE INVENTION

This invention relates to a process for the preparation of aminomethylphosphonates, and more particularly, to the preparation of an N-acylaminomethylphosphonic acid.

N-Substituted-aminomethylphosphonic acids are useful intermediates in the preparation of various products, including sequestering agents and herbicides. Thus, for an example, an N-alkyl-N-phosphonomethylglycine, such as N-isopropyl-N-phosphonomethylglycine, can be dealkylated under alkaline conditions to the corresponding N-phosphonomethylglycine using the method disclosed in EPO Patent Application 86 870 047.7.

N-Phosphonomethylglycine, known also by its common name glyphosate, is a highly effective and commercially important phytotoxicant useful in controlling a large variety of weeds. It is applied to the foliage of a very broad spectrum of annual and perennial grasses and broadleaf plants. Industrial uses include control of weeds along roadsides, waterways, transmission lines in storage areas and in other non-agricultural areas. Usually, N-phosphonomethylglycine is formulated into herbicidal compositions in the form of its various salts in solution, preferably water. The process of the present invention can be used to prepare N-acylaminomethylphosphonic acid, which is useful in the synthesis of N-phosphonomethylglycine.

Numerous methods are known to those skilled in the art for the phosphonomethylation of amides. For example, the disclosure of Miller et al. in U.S. Pat. No. 4,657,705 describes a process for the preparation of an N-substituted aminomethylphosphonic acid, comprising reacting substituted amides with phosphorous acid and formaldehyde in an aqueous acidic medium. Under these conditions the amide is readily hydrolyzed to the free amine prior to phosphonomethylation. N-acylaminomethylphosphonic acids are not isolated or formed in this process.

Pulwer and Balthazor in *Synthetic Communications*, 16(7), 733-739 (1986) report a novel procedure for the preparation of the dimethyl ester of N-benzoylaminomethylphosphonic acid by treating N-hydroxymethylbenzamide with a mixture of phosphorous trichloride and trimethyl phosphite. Hydrolysis of the ester intermediate with acid gave aminomethylphosphonic acid.

U.S. Pat. No. 2,304,156 describes a process for the preparation N-acyl-N-aminomethylphosphonic acid by treatment of a methylol compound with a phosphorus trihalide, and then converting the intermediate ester compound to the phosphonic acid by treatment with water after letting it stand in an enclosed vessel for a long period of time.

Vail, et al., in *Journal of Organic Chemistry*, 27, pp 2067-2070 (June 1962) report that in general, many N-methylol derivatives of the amide type are unstable products which release formaldehyde on heating, whereas the ethers of these derivatives are more stable.

Polish patent application 117780 discloses a method for preparing aminomethylphosphonic acid by reacting phosphorous trichloride with a methylolamide solution in acetic acid and hydrolyzing the reaction mixture. It reports that the reaction is carried out by adding the methylolamide solution to the phosphorous trichloride. It reports that changing the reaction sequence causes an almost complete reaction of methylolamide to give low yields of aminomethylphosphonic acid after hydrolysis.

Oleksyszyn, et al. reported in *Synthesis* (June 1978), pages 479 and 480, a method for the preparation of aminoalkanephosphonic acids in which the aminoalkanephosphonic acid is directly produced from phosphorus trichloride or di-chlorophosphines, carbonyl compounds (aldehydes or ketones) and alkyl carbamates. The reference discloses that the replacement of the carbonyl compounds with the corresponding acetals, as well as replacement of carbamates with simpler amides (e.g. acetamide or benzamide,) resulted in decreased yields.

Despite the prediction of low yields in the prior art and considering the problems associated with handling the unstable methylol derivative, Applicants have now found that N-acylaminomethylphosphonic acids can be produced in high yields and purity from acetamides and benzamides without pre-forming the methylol derivative by the process of the present invention.

SUMMARY OF THE INVENTION

Despite the teachings in the prior art, there is now provided a process for the preparation of N-acyl-aminomethylphosphonic acids represented by the formula

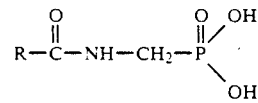

wherein R is selected from the group consisting of methyl and aryl, which comprises:
(a) bringing together under substantially anhydrous reaction conditions an amide represented by the formula

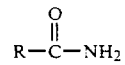

wherein R is as defined above, and paraformaldehyde; and thereafter,
(b) adding phosphorous trihalide to the reaction mixture.

DETAILED DESCRIPTION OF THE INVENTION

The terms methyl and aryl have the usual meanings known to those skilled in the art. The aryl group can be substituted or unsubstituted, and suitable arylamides can be represented by the formula

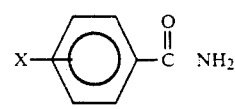

where X is selected from hydrogen, alkyl having one to six carbon atoms, halo, alkoxy having one to six carbon atoms, nitro, or any other group that doesn't interfere with the reaction. Satisfactory results are obtained using the less expensive phenyl group.

The acetamide and benzamide, useful as starting materials in the process of the present invention, can be prepared by techniques known to those skilled in the art. For example, acetyl chloride or benzoyl chloride can be reacted with ammonia to form the corresponding amide. On the other hand, acetic acid or benzoic acid can be condensed with ammonia or a suitable salt to form the corresponding amide.

By the process of the present invention, the acetamide or the benzamide is brought together with paraformaldehyde under substantially anhydrous conditions. This can be achieved by bringing the starting materials together in anhydrous organic acids, such as formic acid and glacial acetic acid. Glacial acetic acid is preferred.

After the acetamide or the benzamide is brought together with the paraformaldehyde in substantially equimolar quantities in the anhydrous organic acid solvent, it is usually necessary to heat the mixture for a short period of time to form a solution. Generally, heating the mixture to between 50° C. and 100° C. for about 30 minutes is sufficient. The time and temperature necessary to form a solution can be readily determined by those skilled in the art.

After the solution of paraformaldehyde and amide has been cooled to below about 30° C., there is then added a slight molar excess of phosphorous trihalide to the reaction mixture. Typical phosphorous trihalides are phosphorous trichloride, phosphorous tribromide and phosphorous triiodide, or mixtures of such halides. Phosphorous trichloride is preferred because of its ready availability.

After the addition of the phosphorous trihalide, the solution is heated to between about 80° C. and about 150° C. for 2 to 4 hours to complete the phosphonomethylation. Temperatures between about 80° C. and 120° C. are preferred. If the temperature exceeds the reflux temperature of the solvent, pressure may be required, as will occur to those skilled in the art.

The N-acyl group can be readily cleaved from the N-acylaminomethylphosphonic acid, if desired, by hydrolysis using a strong mineral acid, such as sulfuric acid or hydrochloric acid. Hydrochloric acid is preferred for acid hydrolysis. On the other hand, the acyl group can be cleaved by a strong base such as an alkali metal hydroxide or carbonate. Sodium hydroxide is preferred for basic hydrolysis. After basic hydrolysis, the product is acidified using a strong mineral acid, such as hydrochloric acid or sulfuric acid, and upon isolation, a high yield of aminomethlyphosphonic acid is obtained.

The invention is further illustrated by, but not limited to, the following examples.

EXAMPLE 1

To a 100 ml flask was charged acetamide (2.95 g, 0.05 mol), paraformaldehyde (1.65 g, 0.055 mol) and glacial acetic acid (35 ml). The mixture was heated to about 100° C. to form a solution. The solution was cooled to room temperature and phosphorous trichloride (7.9 g, 0.058 mol) was added dropwise over a 5 minute period. Then the solution was heated to 110° C. and maintained at this temperature for about 1 hour. The mixture was then cooled to room temperature and water (100 ml) was added. The mixture was then evaporated to an oil under vacuum at 60° C. Analysis by $^{31}$P NMR showed the presence of N-acetylaminomethylphosphonic acid.

The above product was converted to aminomethylphosphonic acid by adding a 50% aqueous solution of sodium hydroxide (22 g, 0.275 mole) and stirring at room temperature for 72 hours. The solution was acidified with concentrated HCl and evaporated to a white solid. The residue was taken up in concentrated HCl (50 ml) and the precipitated sodium chloride was filtered off. The filtrate was evaporated to a white solid and purified by ion exchange chromatography (Dowex 50 x 8-400) using water as the eluent to yield aminomethylphosphonic acid (4.71 g, 84.9% yield).

EXAMPLE 2

The phosphonylmethylation procedure of Example 1 was repeated to prepare N-acetylaminomethylphosphonic acid. After adding water, and evaporating the reaction mixture to an oil, water (25 ml) was added, and the solution was evaporated again to remove residual formaldehyde and formic acid. To the resulting oil was added concentrated hydrochloric acid (60 ml) and the mixture was heated at reflux for about 16 hours. After cooling, the solution was evaporated to an oil and purified by ion exchange chromatography to yield aminomethylphosphonic acid (3.8 g, 68.6% yield).

EXAMPLE 3

A 250 ml flask was charged with benzamide (12.2 g, 0.10 mol) paraformaldehyde (3.2 g, 0.11 mol) and glacial acetic acid (60 ml). The mixture was heated to about 90° C. over a 1 hour period to form a solution. Then, the solution was cooled to room temperature, and phosphorous trichloride (16.4 g, 0.12 mol) was added in one portion, and the solution was heated to 110° C. and held at that temperature for 2 hours. The solution was allowed to cool to room temperature, and water (50 ml) was added to the mixture, which was then evaporated to an oily solid. Analysis by $^{31}$P NMR showed the presence of N-benzoylaminomethylphosphonic acid.

The above product was converted to aminomethylphosphonic acid by adding concentrated hydrochloric acid (100 ml) and heating at reflux for about 16 hours. After purification by ion exchange chromatography, aminomethylphosphonic acid (9.2 g, 82.9% yield) was obtained.

EXAMPLE 4

This example illustrates the poor yields obtained using carbamates. To a 50 ml flask was added methyl carbamate (1.98 g, 0.025 mol) paraformaldehyde (0.79 g, 0.026 mol) and glacial acetic acid (20 ml). The mixture was heated to 85° C. to form a solution and then cooled to about 15° C. in an ice bath. Then, phosphorous trichloride (4.11 g, 0.03 mol) was added in one portion, and the solution was heated to 107° C. over a 1 hour period. After heating at this temperature for about one hour, the solution was evaporated to an oil under vacuum at 60° C. Then, concentrated HCl (50 ml) was added to the solution, and it was heated at reflux for about 14 hours. The mixture was evaporated to a heavy oil again under vacuum at 60° C. Ion exchange purification gave aminomethylphosphonic acid (1.0 g, 36% yield).

Although the invention has been described in terms of specified embodiments which are set forth in considerable detail, it should be understood that this is by way of illustration only, and that alternative embodiments and operating techniques will become apparent to those skilled in the art in view of the disclosure. Accordingly, modifications can be made without departing from the spirit of the described invention.

What is claimed is:

1. A process for the preparation of N-acylaminomethylphosphonic acids represented by the formula

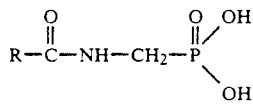

wherein R is selected from the group consisting of methyl and aryl, which comprises:
(a) bringing together under reaction conditions in an anhydrous organic acid an amide represented by the formula

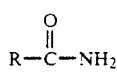

wherein R is as defined above and paraformaldehyde;
(b) adding phosphorus trihalide to form a reaction mixture;
(c) heating the reaction mixture; and thereafter
(d) adding water to form the N-acylaminomethylphosphonic acid.

2. A process of claim 1 wherein the reaction mixture is heated to a temperature between about 80° C. and 150° C.

3. A process of claim 2 wherein the reaction mixture is heated to a temperature between about 80° C. and 120° C.

4. A process of claim 1 wherein the anhydrous organic acid is glacial acetic acid or formic acid.

5. A process of claim 1 comprising the further step of hydrolyzing the N-acyl-aminomethylphosphonic acid to form aminomethylphosphonic acid.

6. A process of claim 5 wherein an aqueous alkali metal hydroxide is used for the hydrolysis.

7. A process of claim 6 wherein the alkali metal hydroxide is sodium hydroxide.

8. A process of claim 5 wherein an aqueous strong mineral acid is used for the hydrolysis.

9. A process of claim 8 wherein the mineral acid is hydrochloric acid or sulfuric acid.

10. A process for the preparation of an N-acylaminomethylphosphonic acid represented by the formula

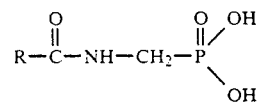

wherein R is selected from the group consisting of methyl and aryl, which comprises:
(a) adding paraformaldehyde and an amide represented by the formula

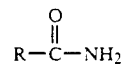

wherein R is as defined above, to glacial acetic acid;
(b) heating the glacial acetic acid containing the amide and the paraformaldehyde to form a solution;
(c) adding phosphorous trichloride to the solution;
(d) heating the solution with the phosphorous trichloride to about 80° C. and about 120° C.

11. A process of claim 10 comprising the further step of hydrolyzing the N-acylaminomethylphosphonic acid with an aqueous alkali metal hydroxide to form aminomethylphosphonic acid.

12. A process of claim 10 comprising the further step of hydrolyzing the N-acylaminomethylphosphonic acid with an aqueous strong mineral acid.

* * * * *